(12) United States Patent
Eaton et al.

(10) Patent No.: US 7,058,439 B2
(45) Date of Patent: Jun. 6, 2006

(54) METHODS OF FORMING PROSTHESES

(75) Inventors: L. Daniel Eaton, Little Rock, AR (US);
John J. Miller, Little Rock, AR (US);
John L. May, Alexander, AR (US)

(73) Assignee: ContourMed, Inc., Little Rock, AR (US)

( * ) Notice: Subject to any disclaimer, the term of this patent is extended or adjusted under 35 U.S.C. 154(b) by 0 days.

(21) Appl. No.: 10/138,735

(22) Filed: May 3, 2002

(65) Prior Publication Data
US 2003/0208269 A1 Nov. 6, 2003

(51) Int. Cl.
*A61B 5/00* (2006.01)
*A61F 2/52* (2006.01)

(52) U.S. Cl. .............................. 600/425; 623/7; 623/8; 623/901

(58) Field of Classification Search .................... 623/7, 623/8, 901; 600/407, 425–427, 429, 476; 356/376; 376/163, 164
See application file for complete search history.

(56) References Cited

U.S. PATENT DOCUMENTS

| | | | |
|---|---|---|---|
| 2,508,156 A | 5/1950 | Gillman | |
| 2,580,264 A | 12/1951 | Wright et al. | |
| 3,021,569 A | 2/1962 | Lyman | |
| 3,065,511 A | 11/1962 | Leitzel | |
| 3,751,540 A | 8/1973 | Prahl, Jr. et al. | |
| 4,086,666 A | 5/1978 | Vaskys et al. | |
| 4,364,880 A | 12/1982 | Howse | |
| 4,401,492 A | 8/1983 | Pfrommer | |
| 4,436,684 A * | 3/1984 | White | 264/138 |
| 4,600,551 A | 7/1986 | Erb | |
| 4,661,187 A | 4/1987 | Beasley | |
| 4,676,795 A | 6/1987 | Grundei | |
| 4,735,754 A | 4/1988 | Buckner | |
| 4,915,757 A | 4/1990 | Rando | |
| 5,108,686 A | 4/1992 | Griffin | |
| 5,140,937 A | 8/1992 | Yamane et al. | |
| 5,169,578 A | 12/1992 | Fukao | |
| 5,249,581 A * | 10/1993 | Horbal et al. | 600/407 |
| 5,376,323 A | 12/1994 | Eaton | |
| 5,455,590 A | 10/1995 | Collins et al. | |
| 5,513,276 A | 4/1996 | Theodoracatos | |
| 5,527,359 A | 6/1996 | Nakamura et al. | |
| 5,557,283 A | 9/1996 | Sheen et al. | |
| 5,700,288 A | 12/1997 | Eaton | |
| 5,776,409 A | 7/1998 | Almquist et al. | |

(Continued)

OTHER PUBLICATIONS

Arkansas Science and Technology Authority News Releases, Nov. 19, 2001.*

(Continued)

*Primary Examiner*—David J. Isabella
(74) *Attorney, Agent, or Firm*—Meyertons, Hood, Kivlin, Kowert & Goetzel, P.C.; Eric B. Meyertons

(57) ABSTRACT

A breast prosthesis may be formed by forming an outer layer on a mold, and filling the mold with a polymerizable foaming composition. The mold may be formed by forming a computer model of the prosthesis based on scanning a patient. The computer model may be used to form a solid model. A prosthesis may be coupled to the patient by coupling at least one metallic insert to the prosthesis and at least one magnet to the patient. Alternately, the prosthesis may be formed with a retaining harness integral to the prosthesis. In still another method, the prosthesis may be coupled to a retaining device surgically implanted in the patient.

30 Claims, 11 Drawing Sheets

U.S. PATENT DOCUMENTS

| | | | |
|---|---|---|---|
| 5,798,062 A | 8/1998 | Thielbar | |
| 5,824,075 A | 10/1998 | Thielbar | |
| 5,855,606 A | 1/1999 | Eaton | |
| 5,859,609 A | 1/1999 | Sheen et al. | |
| 5,870,220 A | 2/1999 | Migdal et al. | |
| 6,074,420 A | 6/2000 | Eaton | |
| 6,086,801 A * | 7/2000 | Eaton | 264/40.1 |
| 6,136,027 A | 10/2000 | Jackson | |
| 6,156,065 A | 12/2000 | Eaton | |
| 6,246,900 B1 * | 6/2001 | Cosman et al. | 600/426 |
| 6,315,796 B1 | 11/2001 | Eaton | |
| 6,405,072 B1 * | 6/2002 | Cosman | 600/426 |
| 6,520,989 B1 | 2/2003 | Eaton | |
| 6,564,086 B1 * | 5/2003 | Marchitto et al. | 600/425 |

OTHER PUBLICATIONS

Contourmed, "Reflecting Nature to Meet Women's Needs", Apr. 2001.*

Company Brochure, ContourMed, Inc., Feb. 2001.

Web Site Pages, www.contourmed.com, ContourMed, Inc., Apr. 2001.

* cited by examiner

METHODS OF FORMING PROSTHESES

BACKGROUND OF THE INVENTION

1. Field of the Invention

The present invention relates to prosthetic devices, methods and systems for forming prosthetic devices, and methods and systems for coupling a prosthetic device to a patient.

2. Description of the Relevant Art

A prosthesis may be used by a patient desiring to augment damaged or deficient anatomy. For example, after a mastectomy, a patient may choose to augment anatomy damaged by the surgery. At its simplest, a breast prosthesis may take the form of external material to be added to the patient's bra. The prosthesis may provide both form and weight to augment the patient's anatomy. A breast prosthesis may be surgically implantable (requiring a surgeon's skill).

Between these two extremes, a custom external breast prosthesis may be formed. The custom prosthesis may be designed to replicate the patient's damaged anatomy. Custom prostheses have been formed by techniques requiring multiple casting steps. In particular, special casting steps may be required to create a custom prosthesis that mirrors a portion of the patient's anatomy. Other methods may require a skilled sculptor to replicate a portion of the patient's anatomy. Additionally, breast prostheses have been formed of various materials. A prosthesis may be formed of materials that allow comfortable use of the prosthesis over an extended period of time. Silicone polymers have been used to produce such prostheses.

Methods of coupling a prosthesis to a patient may include adhesives. For example, one method is to attach the prosthesis directly to the chest of the patient with adhesives. This method may be an uncomfortable solution and may not always be effective. Furthermore, a tight adhesive fit to the chest may trap heat and prevent ventilation of the skin surface. Another common method is to place the prosthesis in a pocket of a bra. This method may also present concerns since the prosthesis may shift out of position within the bra.

SUMMARY OF THE INVENTION

In an embodiment, a model of a breast prosthesis may be formed by providing a scanning system. The scanning system may include at least one imaging device, and at least one alignment marker. At least one alignment marker may be arranged with respect to a patient and within the field of view of the imaging device. A first set of data elements may be determined using the scanning system. The first set of data elements may be based on the patient's breast while the patient's breast is at least partially covered by a garment (e.g., a bra or a swimsuit). A computer model of a breast prosthesis may be determined based on the first set of data elements. At least one alignment marker may be used to determine alignment of the computer model.

In an embodiment, a computer program may receive the first set of data elements determined by scanning the patient. The first set of data elements may correspond to a first surface. A second set of data elements may be determined based on the first set of data elements. The second set of data elements may correspond to a second surface. The second surface may be a mirror image of the first surface. The computer program may be further configured to receive a third set of data elements determined by scanning the patient over an area including at least the patient's surgical site. The third set of data elements may correspond to a third surface. The third surface may represent the patient's chest in an area including the surgical site. A computerized model of a breast prosthesis may be determined based on the second set of data elements, the third set of data elements and/or a combination of the two. The computer program may send a signal to a rapid prototyping system based on the computerized model of the breast prosthesis. The signal may provide instructions to the rapid prototyping system for generating a model of the breast prosthesis. The model of the breast prosthesis may be used to form a mold for casting a breast prosthesis.

In an embodiment, a breast prosthesis may be formed by forming an outer layer on at least a portion of the interior of a mold. The outer layer may be formed by applying at least one layer of a polymerizable composition to at least a portion of the interior of the mold. After forming the outer layer, at least a portion of the mold may be filled with a polymerizable foaming composition. The mold may be assembled to inhibit the polymerizable foaming composition from expanding beyond the mold. The polymerizable foaming composition may be cured. The polymerizable foaming composition may be removed from the mold. The outer layer may be coupled to the cured foaming composition. The posterior portion may have a shape configured to conform to a portion of a chest wall of a patient.

In an embodiment, the posterior portion may include a textured surface. The textured surface may be formed by applying a polymer layer to a mold having a textured surface. The mold having the textured surface may be formed by applying a polymerizable solvent composition to a substrate. The polymerizable solvent composition may at least partially dissolve the surface of the substrate as it cures, providing a textured surface to the polymerizable solvent composition. The cured polymerizable solvent composition may be used to form a textured mold.

In an embodiment, a prosthesis may be coupled to a patient by coupling at least one metallic insert to the prosthesis. At least one magnet may be adhered to the patient. At least one magnet adhered to the patient may be aligned with at least one metallic insert of the prosthesis. For example, at least one magnet may be placed in an adhesive backed pouch. The prosthesis may be coupled to the patient such that at least one magnet and at least one metallic insert are aligned sufficiently to retain the prosthesis in position relative to the patient.

In another embodiment, a prosthesis may be coupled to a patient by a retaining harness integral with the prosthesis. The retaining harness may extend around the neck of the patient. The retaining harness may be formed of the same material as the outer layer of the prosthesis. The harness may further include an opening through which an intact breast may project.

In an embodiment, a breast prosthesis may include a plurality of chambers. At least one chamber may include a gel. At least one chamber may include a foam material. At least one layer of a polymer may separate at least two chambers. Additionally, at least one chamber may include air.

In still another embodiment, a prosthesis may be retained by a surgically implanted retaining device. The surgically implanted retaining device may include a flange, a percutaneous abutment, a fixation connector, a fixture mount, and a retaining connector.

BRIEF DESCRIPTION OF THE DRAWINGS

Other objects and advantages of the invention will become apparent upon reading the following detailed description and upon reference to the accompanying drawings in which.

Figure 1:
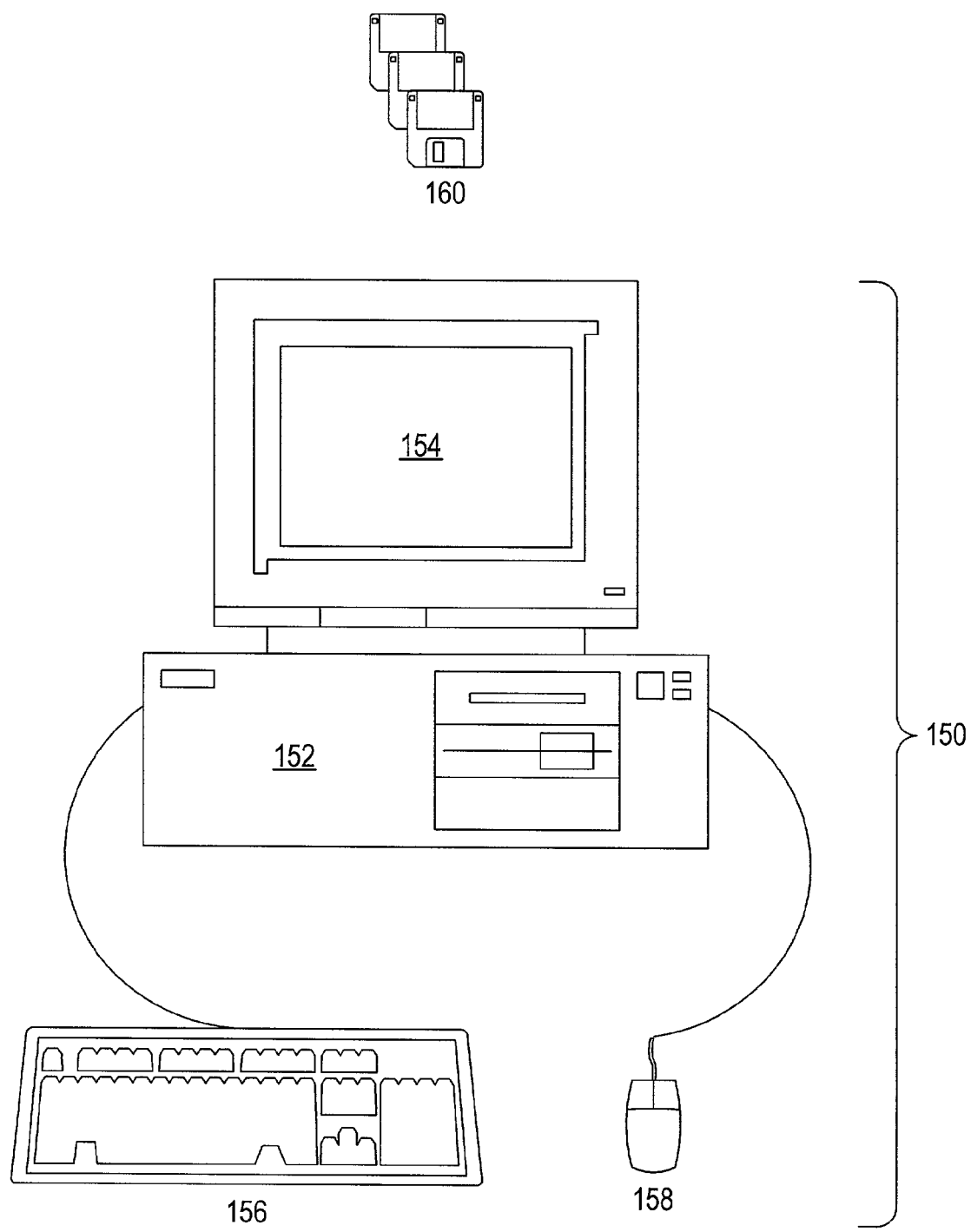
FIG. 1 depicts an embodiment of a computer system.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Embodiments disclosed herein generally relate to prostheses, and methods and systems of forming prostheses. The embodiments are generally described in terms of breast prostheses; however, it is recognized that methods and systems described herein may be used to form a variety of prostheses, and are not limited to breast prostheses.

Prostheses and methods of forming prostheses are disclosed in U.S. Pat. No. 5,376,323 to Eaton, U.S. Pat. No. 5,700,288 to Eaton, U.S. Pat. No. 5,798,062 to Thielbar, U.S. Pat. No. 5,855,606 to Eaton, U.S. Pat. No. 6,074,420 to Eaton, U.S. Pat. No. 6,086,801 to Eaton, U.S. Pat. No. 6,136,027 to Jackson, U.S. Pat. No. 6,156,065 to Eaton, U.S. Pat. No. 6,315,796 to Eaton and U.S. Pat. No. 6,520,989 to Eaton, each of which is incorporated herein by reference as though fully set forth herein. Methods of forming computer models of three dimensional objects are disclosed in U.S. Pat. No. 5,455,590 to Collins et al, U.S. Pat. No. 5,513,276 to Theodoracatos, U.S. Pat. No. 5,557,283 to Sheen et al., U.S. Pat. No. 5,859,609 to Sheen et al., and U.S. Pat. No. 5,870,220 to Migdal et al. each of which is incorporated herein by reference as though fully set forth herein. Methods of forming solid models using computer-controlled devices are disclosed in U.S. Pat. No. 4,915,757 to Rando, U.S. Pat. No. 5,140,937 to Yamane et al., U.S. Pat. No. 5,776,409 to Almquist et al., each of which is incorporated herein by reference as though fully set forth herein.

FIG. 1 illustrates an embodiment of computer system 150 that may be suitable for implementing various embodiments disclosed herein. Each computer system 150 typically includes components such as central processing unit (CPU) 152 with an associated memory medium such as floppy disks 160. The memory medium may store program instructions for computer programs. The program instructions may be executable by CPU 152. Computer system 150 may further include a display device such as monitor 154, an alphanumeric input device such as keyboard 156, and a directional input device such as mouse 158. Computer system 150 may be operable to execute one or more computer programs to acquire an image of an anatomical feature of a patient, to manipulate an image of an anatomical feature of a patient and/or to control a rapid prototyping system.

Computer system 150 may include a memory medium on which computer programs according to various embodiments may be stored. The term "memory medium" is intended to include an installation medium (e.g., a CD-ROM or floppy disks 160), a computer system memory (e.g., DRAM, SRAM, EDO RAM, Rambus RAM, etc.), or a non-volatile memory (e.g., magnetic media, or optical media). The memory medium may also include other types of memory or combinations thereof. In addition, the memory medium may be located in a first computer which executes the programs or may be located in a second different computer which connects to the first computer over a network. In the latter instance, the second computer may provide the program instructions to the first computer for execution. Computer system 150 may take various forms such as a personal computer system, mainframe computer system, workstation, network appliance, Internet appliance, personal digital assistant ("PDA"), television system or other device. In general, the term "computer system" may refer to any device having a processor that executes instructions from a memory medium.

The memory medium may store a software program or programs operable to implement embodiments disclosed herein. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes ("MFC"), browser-based applications (e.g., Java applets), traditional programs, or other technologies or methodologies, as desired. A CPU such as host CPU 152 executing code and data from the memory medium may include a means for creating and executing the software program or programs according to the embodiments described herein.

Figure 2:
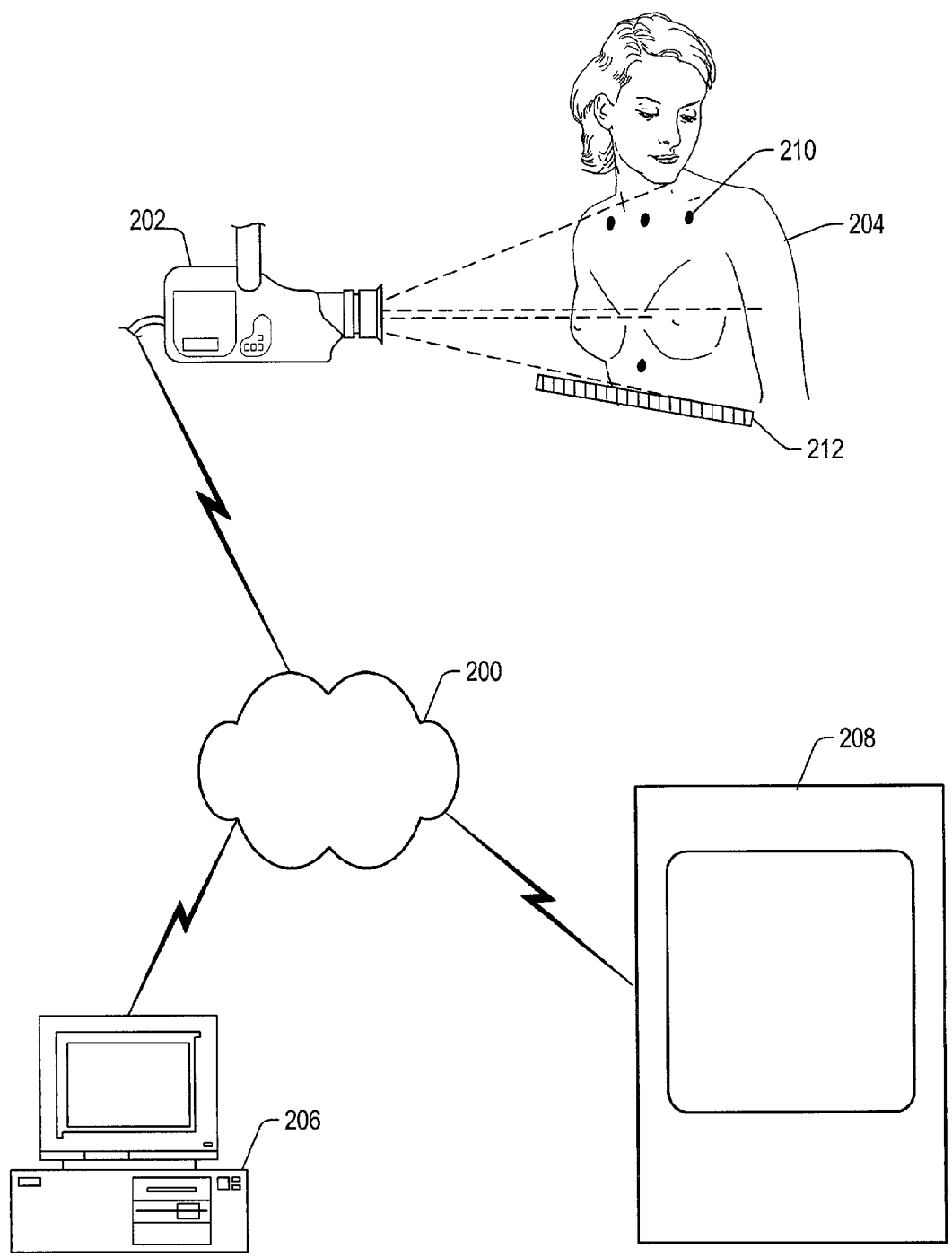
FIG. 2 depicts an embodiment of a system for forming a model of a breast prosthesis.

FIG. 2 illustrates a network 200 according to one embodiment. In an embodiment, network 200 may include a wide area network (WAN) or a local area network (LAN). A WAN refers to a network that spans a relatively large geographical area. The Internet is an example of a WAN. A WAN typically includes a plurality of computer systems that may be interconnected through one or more networks. Although one particular configuration is shown in FIG. 2, a WAN may include a variety of heterogeneous computer systems and networks that may be interconnected in a variety of ways and that may run a variety of software applications.

A LAN refers to a network that spans a relatively small area. Typically, a LAN may be confined to a single building or group of buildings. One or more LANs may be coupled to WAN. Each node (i.e., individual computer system or device) of a network may have its own CPU with which it may execute programs, and each node may also be able to access data and devices elsewhere on the network. A network may be characterized by a variety of types of topology (i.e., the geometric arrangement of devices on the network), of protocols (i.e., the rules and encoding specifications for sending data, and whether the network uses a peer-to-peer or client/server architecture), and of media (e.g., twisted-pair wire, coaxial cables, fiber optic cables, and/or radio waves).

As illustrated in FIG. 2, two or more devices configured to carry out methods described herein may communicate via a network 200. For example, a scanning system 202 may gather information regarding a patient 204. Scanning system 202 may include an imaging device. In an embodiment, scanning system 202 may also include a computer system. In an alternate embodiment, an imaging device of scanning system 202 may provide image information to computer system 206 without an intermediate computer system. Scanning system 202 may provide at least some of the gathered information to a computer system 206. In various embodiments, information may be provided to computer system 206 via a removable memory medium (e.g., a CD-ROM) or via network 200. Computer system 206 may include one or more software applications executable to manipulate graphical information. For example, a software application available on computer system 206 may provide a graphical display of a computer model based on the information provided by scanning system 202. In addition, a software application available on computer system 206 may be executable to manipulate a computer model. In an embodiment, the software application may be executable to manipulate data elements of the computer model. For example, the software application may determine if one or more data elements are missing (e.g., from data corruption or imperfections in the scanning process). If one or more data elements are determined to be missing, the software application may approximate the position of the missing data elements (e.g., to provide a continuous surface on the computer model). In another example of manipulating the data elements of the computer model, the software application may be executable to remove certain data elements. For example, since a scanning process may be conducted while the patient's breast is at least partially covered by a garment (e.g., a bra or swimsuit), the software application may be executable to remove data elements associated with the garment. In such a case, the removed data elements may be replaced with data elements approximating the surface of the breast. In addition, computer system 206 may include at least one software application executable to determine a mirror image of a computer model. Computer system 206 may also include at least one software application executable to combine two or more computer models into a single computer model.

Computer system 206 may provide information regarding a computer model to a rapid prototyping system 208. In various embodiments, information regarding the computer model may be provided to computer system 206 via a removable memory medium (e.g., a CD-ROM) or via network 200. Rapid prototyping system 208 may include at least one manufacturing device for forming a solid model substantially corresponding to the computer model. Rapid prototyping system 208 may include a computer system configured to convert information regarding the computer model into a control signal to be sent to at least one solid model forming device. Alternately, computer system 206 may send the information regarding the computer model to rapid prototyping system 208 in the form of a control signal.

Various embodiments may also include receiving or storing instructions and/or data implemented in accordance with the foregoing description upon a carrier medium. Suitable carrier media may include storage media or memory media such as magnetic or optical media, (e.g., a hard-disk or CD-ROM). Suitable carrier media may also include signals such as electrical, electromagnetic, optical signals (whether digital or analog). Such signals may be conveyed via a communication medium such as network 200 and/or a wireless link.

In an embodiment, the arrangement depicted in FIG. 2 may allow patient's to be seen in a different facility than computer model production and/or solid model production. For example, patients may be seen at remote locations while computer and/or solid models are produced at a central manufacturing location. In such an example, scanning system 202 may be portable. Thus, scanning system 202 may be relocated to various remote locations as desired to conveniently provide services to patients. In an embodiment, both scanning system 202 and computer system 206 may be portable. Such an embodiment may allow patients to be scanned at remote locations. After scanning, a patient may be allowed to view a computer model of a prosthesis. Such embodiments may allow a patient to make more informed decisions regarding the prosthesis to be formed.

In an embodiment, a method forming a prosthesis may begin by gathering background information regarding a patient expected to utilize the prosthesis. For example background information gathered may include, but is not limited to: marketing-related information, medical history information, descriptive information regarding the patient, information regarding the desired prosthesis, etc. The background information may be helpful to prepare a custom prosthesis for the patient or to select an appropriate non-custom prosthesis. The medical history information may include, but is not limited to: location of mastectomy (e.g., right, left or bilateral), date of mastectomy, location of sensitive areas associated with the mastectomy (e.g., sensitive scar tissues), sensitivities to various materials (e.g., adhesives), etc. Information gathered regarding the desired prosthesis may include, but is not limited to: desired characteristics of the prosthesis (e.g., light weight, realistic feel, etc.), size, nipple design and color, prosthesis color, etc. Descriptive information gathered about the patient may include, but is not limited to: skin complexion information (e.g., skin tone, presence of freckles, etc.), bra size and style, etc.

In an embodiment, additional descriptive information regarding the patient may be gathered using one or more imaging devices of scanning system 202. The descriptive information gathered by scanning system 202 may be used to generate a computer model of portions of the patient's anatomy. FIG. 2 depicts an embodiment of a scanning system 202 in relation to a patient 204. An imaging device of scanning system 202 may include any of a plurality of different devices for gathering geometric data to describe a surface or three-dimensional object. Examples of suitable devices may include, but are not limited to: sonic or ultrasonic imaging devices, laser scanning devices and electromagnetic (EM) wave imaging devices (e.g., a millimeter wave scanner). As used herein, a "millimeter wave" refers to electromagnetic radiation having a frequency between about 1 gigahertz and about 300 gigahertz. Suitable imaging devices are commercially available from Minolta Corporation USA of Ramsey, N.J. and Tracer Corporation of Boca Raton, Fla. In an embodiment where a patient has at least one intact breast, scanning system 202 may be used to gather geometric data regarding the intact breast. For example, if a patient has an opportunity to prepare a prosthesis before a mastectomy, the patient may have both breasts intact. In such a case, both of the patient's breasts may be scanned. In a more typical example, a patient may seek a prosthesis after having a mastectomy. In such a case, if the patient has an intact breast, the intact breast may be scanned. As used herein, "scanning" refers to the process of gather geometric data regarding a portion of the patient's anatomy. Scanning results in the creation of a set of data elements representing the scanned surface. For example, the data elements may represent the surface of the patient's breast and/or the surface of a garment covering the patient's breast. The set of data elements from the scan may be used in embodiments disclosed herein to form a breast prosthesis.

In an embodiment, scanning the patient's anatomy may include having the patient at least partially disrobe. Since a breast prosthesis is typically worn with a bra, it may be desirable for the prosthesis to have a shape corresponding to the shape of the patient's breast while supported by a properly fitting bra of the style preferred by the patient. Thus, scanning may be performed while the patient is wearing a properly fitted bra or similar garment (e.g., a swimsuit). Alternately, in an embodiment, a patient may desire a prosthesis that can be worn without a bra. In such a case, a scan of the patient's bare breast may be performed. A number of alignment markers 210 may be put on the patient to allow a computer model to be generated from the scan that includes proper alignment information. For example, alignment markers may be placed on the patient directly below the supra sternal notch, directly below the xiphoid process and on each bilateral clavicular head. These anatomical features are convenient alignment points; however, it is recognized that other alignment points could be used. As used herein, an "alignment marker" refers to an object that is noticeable in a scanned image and may be used in manipulating the scanned image as a reference point. For example, alignment markers may include any object that reflects the scanning medium in a significantly different manner than the patient's skin and/or a garment worn by the patient. Examples of suitable alignment markers include, but are not limited to: adhesive-backed members of a variety of shapes and sizes. For example, commercially available, self-adhesive paper or foam dots have been found to be useful as alignment markers. The patient may be positioned in the field of view of at least one imaging device of scanning system 202. Additionally, an orientation marker 212 may be positioned in the field of view of the imaging device. As used herein, an "orientation marker" refers to a device used to assist a scanner operator in orienting the scanning system with regard to the patient. Alternatively, an orientation marker may be a device used to assist in orienting the patient with respect to a fixed scanning system. For example, an orientation marker may assist the operator in orienting the imaging device and/or patient approximately normal to an imaginary front surface plane of the patient. That is, the orientation marker may be used to determine whether the imaging device is at an angle with respect to the patient. The patient may stand between the orientation marker and a wall. The patient's posture may be checked to ensure that the patient is roughly parallel to the wall. For example, the patient's elbows, shoulders and/or buttocks may be positioned so that they touch the wall. The orientation marker may be placed in front of the patient. Measurements may be taken to ensure that the orientation marker is substantially level and parallel to the wall. Thus, if the orientation marker is skewed in the scanned image, it may be assumed that the imaging device was not properly oriented with respect to the patient and undesired perspective may have been introduced into the scanned image. The image scanning may be repeated. Alternately, the scanned image of the orientation marker may be used by a graphics manipulation software application as described below to remove the undesired perspective.

After a mastectomy, the patent's chest may be scanned in an area that includes the surgical site. It may be desirable to postpone scanning the patient's surgical site until sufficient time has elapsed since the surgery for swelling to substantially subside. Scanning the surgical site may form a set of data elements corresponding to the surface of the patient's chest in the area where the prosthesis will be worn. In addition to the scans of the patient's anatomy, one or more photographs of the patient may be taken. Once the background information, including scans, has been collected, it may be saved and filed for use during modeling and production of the prosthesis.

Figure 3:
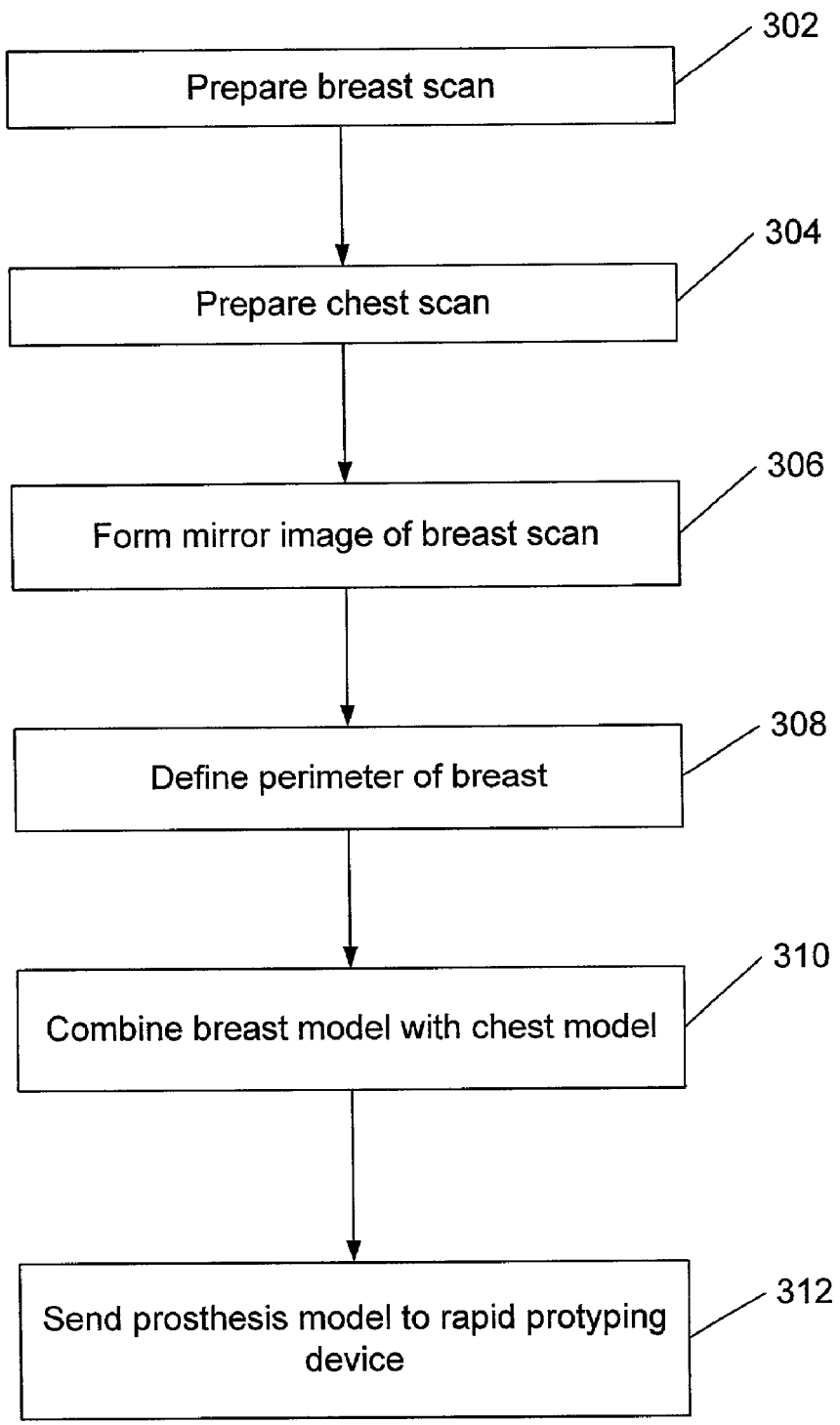
FIG. 3 depicts a flowchart of an embodiment of a method of forming a model of a breast prosthesis.

Data elements from scanning the patient's anatomy may be provided to computer system 206 for formation of an electronic model of the desired breast prosthesis. FIG. 3 depicts a flowchart of an exemplary embodiment of a method of forming a model of a breast prosthesis. In boxes 302 and 304, the breast scan data and surgical site scan data may be prepared. To prepare the scan data, the data may be provided to a graphical imaging software application. For example, a commercially available computer aided design or computer aided modeling (CAD/CAM) software application with three-dimensional modeling capabilities may be used. Software applications are available from TracerCAD, and Raindrop Geomagic of Research Triangle Park, N.C. The graphical imaging software application may be used to form a computer model of the scanned areas. As used herein, a "model" refers to a physical or graphical representation of an object. The scan data may be filtered to identify portions of the data that are missing and/or corrupted. Known techniques may be used to interpolate or otherwise adjust for missing and/or corrupted data. Preparing the scan data may also include identifying the alignment markers in the computer models. At box 306, a reflection transformation may be applied to the breast computer model to form a mirror image of the breast computer model. Thus, if the patient's right breast was scanned, the reflection transformation may create a left breast that is an exact duplicate of the right breast but oriented for the patient's left side. The perimeter of the breast computer model may be identified at box 308. Identifying the perimeter of the breast computer model may establish the edge of the form and allow a depth measurement to be made to ensure symmetry. The breast model and surgical site model may be combined at box 310. In the combined model, the breast model may form the anterior surface while the surgical site model forms the posterior surface. Thus, a complete electronic model of a breast prosthesis is formed wherein the front of the breast prosthesis mirrors the shape of the patient's intact breast and the back of the prosthesis is custom fit to the patient's surgical site. In an embodiment, the computer model of the breast prosthesis may be manipulated to form desired features and/or removed undesired features. For example, since a patient's breast may be scanned while the breast is at least partially covered by a garment, the computer model may be adjusted to have a shape approximating the shape of the patient's breast inside the garment. For example, seam lines may be removed and/or physical characteristics not clear through the garment (e.g., the nipple region) may be added. In another example, the back of the prosthesis computer model may be adjusted to provide additional clearance over sensitive areas to ensure that the actual prosthesis will not contact these areas. In yet another example the back of the prosthesis computer model may be provided with a textured surface.

In the case of a patient who had a breast scanned before a mastectomy was performed, the reflection transformation may be omitted. Thus, the front of a formed prosthesis may match the removed breast, while the back of the prosthesis may be matched to the patient's surgical area. In the case of a patient with no intact breast to scan (e.g., after a bilateral mastectomy), several different methods may be used to provide suitable prostheses. In a first embodiment, two breast prosthesis models may be selected from a database computer models. For example, at least some of the breast computer models formed by methods described above may be stored in a computer memory. In such a case, these breast computer models may be available for review by patients to select one or more desired breast computer models. The selected breast computer model or models may be combined with scans of the patient's surgical sites to form two custom prosthesis computer models. In a second embodiment, the patient may be scanned while wearing a bra. At least one cup of the bra may be filled with any suitable material to form the cup into a desired shape. The filled bra cup may be scanned. A computer model of the scanned bra cup may be used along with scans of the patient's surgical areas to form two prosthesis computer models. In such a case, the reflection transformation step may be used in forming only one of the prosthesis computer models.

A computer model of a breast prosthesis may be used to control rapid prototyping system 208. As used herein, "rapid prototyping" may refer to computer controlled formation of a solid model. Examples of rapid prototyping systems may include, but are not limited to: computer numerical controlled (CNC) milling systems, stereo lithography systems, laser sintering systems, etc. Rapid prototyping systems are commercially available from a variety of manufacturers. Such systems may include a manufacturing device for forming a solid model and one or more computer systems for controlling the manufacturing device. A set of data elements corresponding to a computerized model may be provided to rapid prototyping system 208, resulting in the formation of a solid model of a breast prosthesis. For example, a CNC milling machine may be used to form a breast prosthesis model out of a polyurethane blank.

A breast prosthesis model formed by a rapid prototyping system may require hand finishing. For example, some rapid prototyping methods may form slightly uneven surfaces, which may be sanded to create smooth surfaces. Once a satisfactory solid model has been formed, the model may be used to form a mold for the breast prosthesis. The solid model may be divided into a breast portion and a surgical site portion. The nipple region of the breast model may be marked. A mold release agent may be applied to the breast model and to the surgical site model. The breast model may be placed in a mold forming box. The mold forming box may have an adjustable size to accommodate prosthesis models of varying sizes.

A mold forming composition (e.g., plaster) may be used to form a mold around the prosthesis model. For example, a mixture of water and white orthodontic stone has been found to be a suitable mold forming composition. The orthodontic stone may be acquired as a powder, which may be mixed (e.g., with an handheld electric mixer) with water to a suitable consistency. For example, a mixture in the ratio of about 28 ml water per 100 grams of orthodontic stone has been found to create a suitable consistency. After mixing, the mold forming composition may be allowed to sit for a period of time to allow some air to escape and to allow catalysis of the composition to begin. The mold forming composition may be poured into the mold forming box such that the entire breast model is covered. The surgical site model may be coated with the mold forming composition to form the back mold. The mold forming composition may be allowed to harden. When the mold forming composition is substantially hardened, the breast model and surgical site model may be removed from the mold forming composition, leaving behind the desired molds. The molds may be hand sanded, and imperfections in the surface of the molds may be filled so that a smooth surface is formed. The molds may be allowed to continue to cure for a period of time (e.g., about 5 days).

Figure 4:
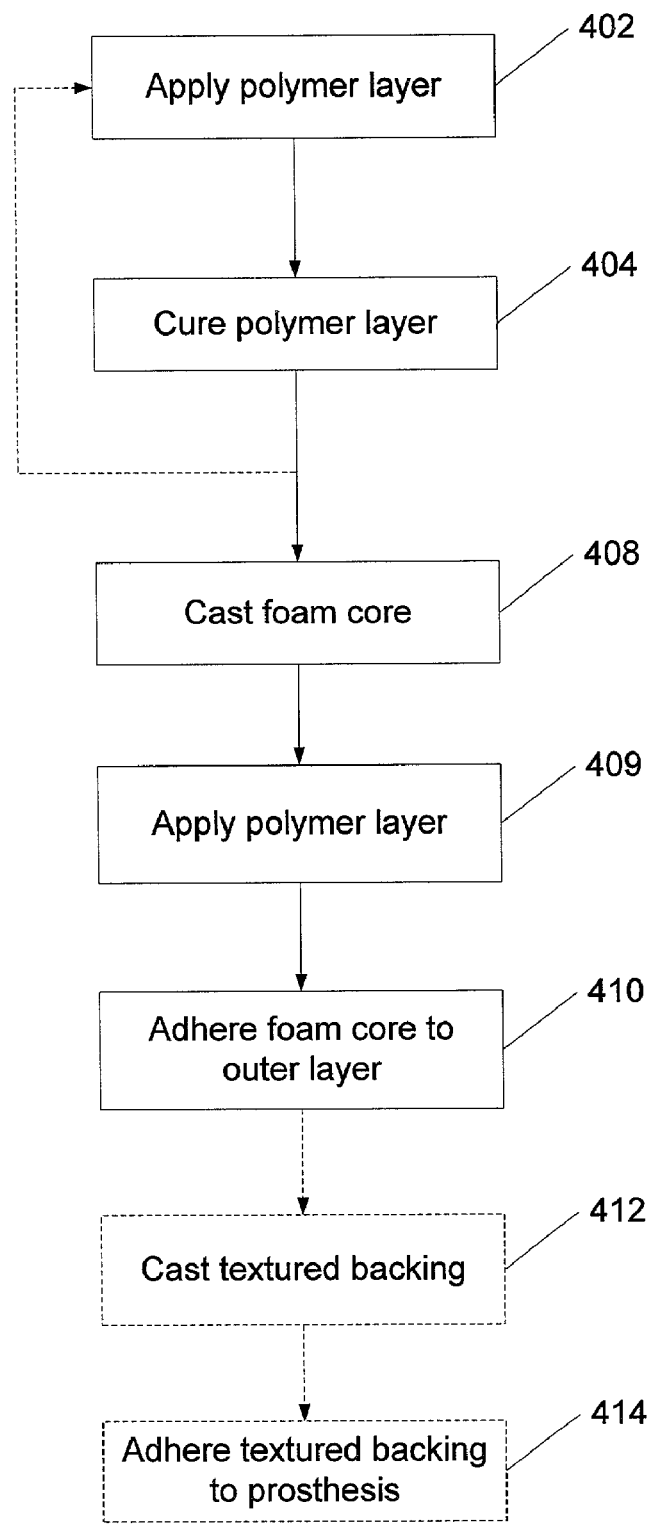
FIG. 4 depicts a flowchart of an embodiment of a method of forming a breast prosthesis.
Figure 5:
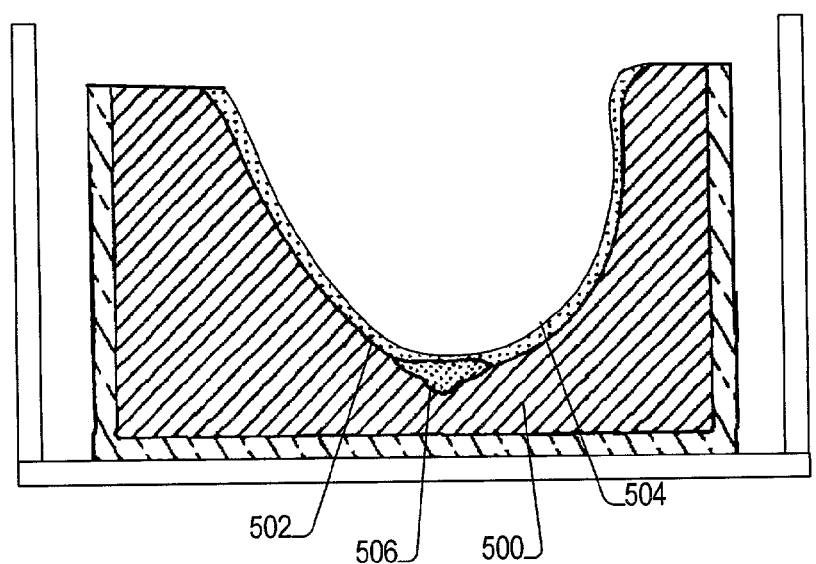
FIG. 5 depicts an embodiment of a breast prosthesis mold.
Figure 6:
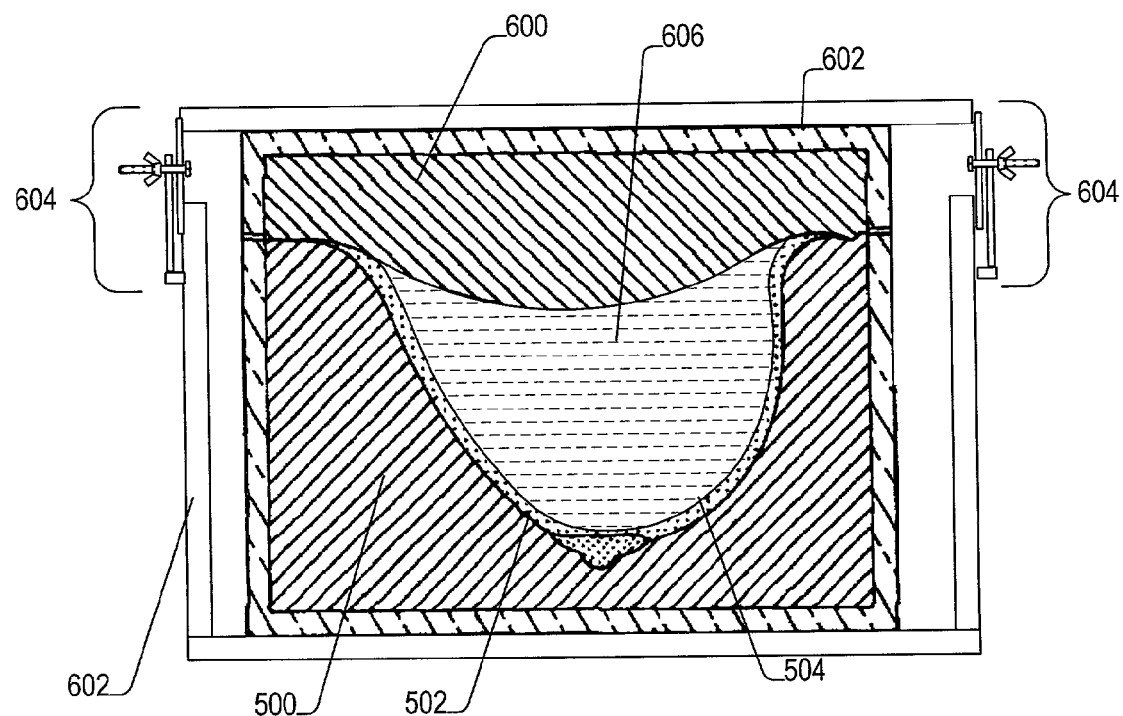
FIG. 6 depicts an embodiment of a breast prosthesis mold in a molding box.

When the molds are ready, the prosthesis casting process may begin. A flowchart of an embodiment of a breast prosthesis casting process is depicted in FIG. 4. In addition, FIGS. 5 and 6 depict cut away views of a breast prosthesis mold during the forming process.

An outer layer 502 may be formed on at least a portion of the interior of the mold. Outer layer 502 may be formed of one or more polymer layers. A layer of a polymer may be formed on the interior of mold 500 by applying a polymerizable composition to mold 500 (see box 402 of FIG. 4), and curing the polymerizable composition (see box 404 of FIG. 4). In various embodiments, the polymerizable composition may be sprayed and/or brushed onto the mold. The polymerizable composition may include any of a number of commercially available polymers that may form soft, non-irritating layers. For example, silicone polymers are useful in this regard. For example, LIM 6010 silicone, commercially available from GE Silicones of Waterford, N.Y. may be used. LIM 6010 is a two-part composition including LIM 6010A and LIM 6010B. Approximately equal parts LIM 6010A and LIM 6010B may be mixed together. A portion of toluene or another suitable solvent may be added to the mixture as a thinning agent. For example if the polymerizable composition is to be spray coated over the interior of the mold about 95 grams of toluene may be added per 100 grams of LIM 6010.

In an embodiment, the layer of polymer may then be colored by applying a coloring agent. For example, a silicone dispersion having the desired color may be used as a coloring agent. A coloring agent mixed into a polymerizable composition may be brushed or sprayed over at least a portion of the interior of the polymer layer. The region of the polymer layer corresponding to the nipple 506 may be colored differently than the balance of the polymer layer to provide a more realistic appearance. The nipple color and breast color may be selected and/or mixed to approximate the patient's skin tone and complexion based on photographs and/or other background information. Applying a layer of a polymerizable composition and curing the layer may be repeated until a desired thickness of the outer layer is established (e.g., about 5 layers). As used herein, the "outer layer" refers to one or more polymer layers that form the exterior (or "skin") of the prosthesis. In an alternate embodiment, only the first polymer layer of the outer layer may be applied then colored. Remaining layers of the outer layer may be applied with a coloring agent mixed into the polymerizable composition before application. For example, in a mixture of the ratio of about 100 grams of LIM 6010 to about 95 grams of toluene, about 12 grams of coloring agent may be added for the remaining layers of the outer layer.

The back mold 600 and front mold 500 may be assembled in a molding box 602 to cast a foam core 606 (see box 408 of FIG. 4). Molding box 602 may align the molds and retain them in position during casting of the breast prosthesis. Molding box 602 may include adjustable clamps 604 to retain the molds in position. A foaming polymerizable composition may be placed in the mold assembly. For example, a foaming polyurethane composition may be used. A suitable foaming polymerizable composition may include, a mixture in the ratio of about 25 grams of 25880R elastoflex and about 9.5 grams of Isocyanate 25840T, both commercially available from BASF Corporation of Mount Olive, N.J. may be used. The mixture may be prepared by mixing the two components quickly and thoroughly with a high-speed electric mixer. The mixture may then be poured into front mold 500. Back mold 600 may be positioned relative to front mold 500 and molding box 602 may be closed and clamped shut. Molding box 602 may restrain the expansion of the foam. The foaming polymerizable composition may be allowed to cure (e.g., for about 5 minutes).

After curing, foam core 606 may be removed from molding box 602. The foam may be hand trimmed and shaped (e.g., sanded) as needed to form the core of the breast prosthesis. In an embodiment, a coloring agent may be applied to the foam core. The coloring agent may, for example, be sprayed or brushed onto the foam core. In such an embodiment, a number of layers of the coloring agent may be applied to the foam core depending on the particular coloring agent used, and the desired final color of the core. In multilayer coloring processes, the coloring agent may be allowed to cure between layers. In an embodiment, one or more additional polymer layers may be brushed or sprayed on at least a portion of the interior of the mold after the foam core is removed from the mold (see box 409 of FIG. 4). Additional polymer layers may be added until a desired thickness of the outer layer is reached (e.g., about 9 additional layers).

In an embodiment, the foam core may be coupled to outer layer 502 of the prosthesis (see box 410 of FIG. 4). An additional layer of a polymer may be used to adhesively couple the foam core to the outer layer. The additional polymer layer may include a coloring agent. For example, Dow Corning 732 silicones (commercially available from Dow Corning Corporations of Midland, Mich.) may be mixed with a coloring agent and applied either to the foam core or to the outer layer. The foam core may then be inserted into the outer layer. Pressure may be applied to ensure that the outer layer adheres evenly to the foam core. For example, molding box 602 may be reassembled and clamped together while the additional polymer layer cures. Alternately, the outer layer may be removed from the mold and carefully placed over to the foam core. Even pressure may be applied to the outer layer by hand to provide substantially even adhesion to the core.

In an embodiment, the back of the foam core may be covered with another layer of a polymerizable composition. In an embodiment, the same composition as used for the outer layer may be used to cover the back of the foam core. For example, a layer of the polymerizable composition may be brushed or sprayed over the back surface of the foam core. In an embodiment, the mold clamping box may again be closed and clamped while the polymerizable composition cures.

The breast prosthesis may be removed from the mold by carefully loosening the outer layer from the mold. In an embodiment, a textured backing may be adhered to the prosthesis as described below. The prosthesis may be trimmed and the edges may be beveled and smoothed. Additionally, any imperfections may be filled using the polymerizable composition used to form the outer layer.

In an embodiment, a textured back surface may be added to a breast prosthesis (see box 414 of FIG. 4). As used herein, a "textured surface" refers to a surface that is not smooth. For example, a textured surface may be rough. In another example, a textured surface may include topography configured to reduce the contact area between the patient and the prosthesis (e.g., to improve ventilation) and/or to provide tactile feedback to the patient regarding the position of the prosthesis. A textured surface may include, but is not limited to: a surface having a predetermined, arbitrary or random pattern. For example, a pattern may be created on the surgical site mold by altering the surgical site mold or by altering the computer model of the surgical site. In an embodiment, a random pattern may be formed on the textured back surface by casting the textured back surface using a textured mold (see box 412 of FIG. 4). In an embodiment, textured mold may be formed by a method described with reference to FIG. 7.

Figure 7:
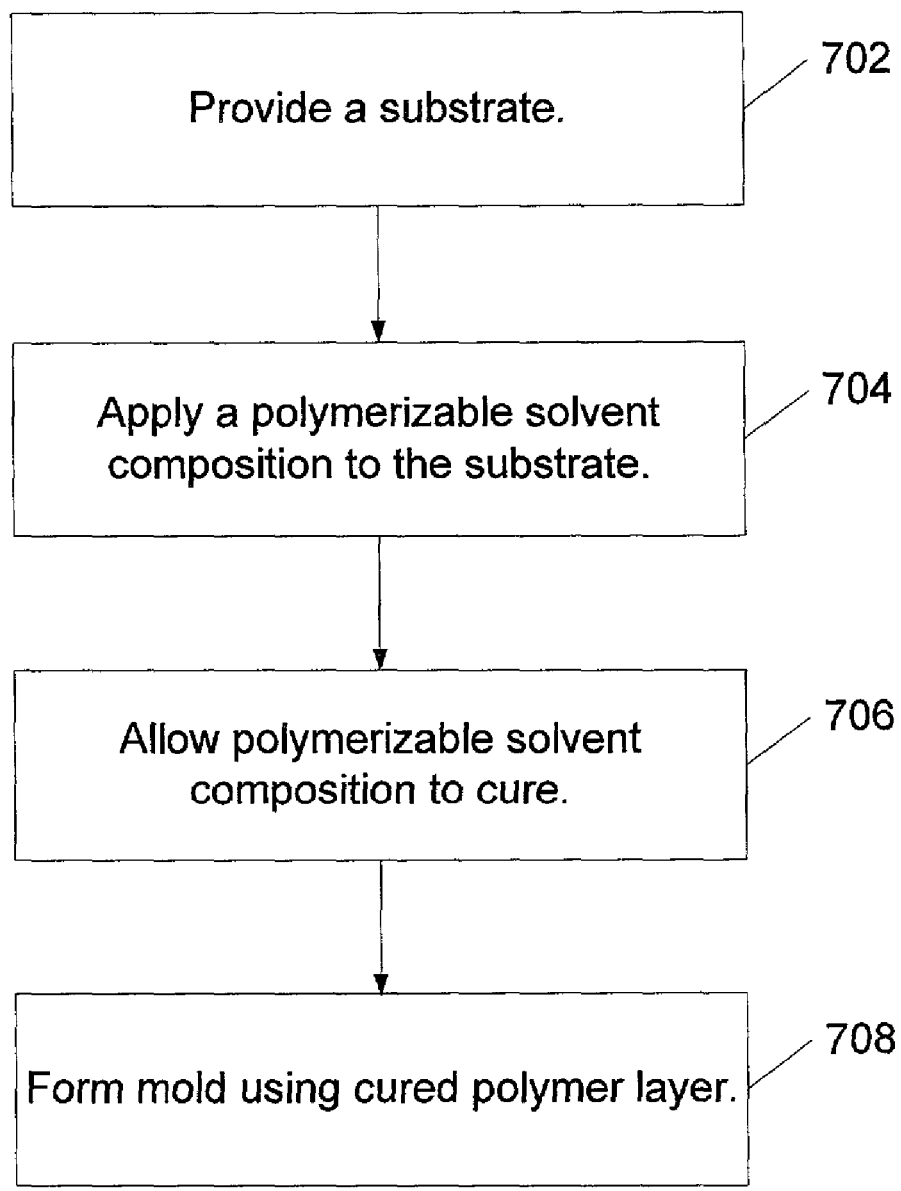
FIG. 7 depicts a flowchart of a method of forming a mold for casting a textured backing.

FIG. 7 depicts a flow chart of a method of forming a mold including a textured surface. A substrate may be provided at box 702. The substrate may be formed of a material that is at least partially soluble in a polymerizable solvent composition. For example, the substrate may include polyurethane or polyethylene foam, and the polymerizable solvent composition may include methyl methacrylate. At box 704, the polymerizable solvent composition may be applied to the substrate. The polymerizable composition may react with the substrate to at least partially dissolve the substrate. The polymerizable composition may cure to form a textured surface at box 706. The textured surface may be cleaned to remove residue of the substrate. The textured surface may be used to form a mold at box 708.

A polymerizable composition may be applied to a textured positive mold to form a textured backing for a prosthesis. In an embodiment, the same composition used to form the outer layer may be used. It has been found through experimentation that a mixture of about 3 parts LIM 6010A to about 1 part LIM 6010B, or more specifically, about ratio of about 76 grams of LIM 6010A to 26 grams of LIM 6010B, may have desirable characteristics for a textured back. The polymerizable composition may be applied to the textured mold (e.g., by brushing, spraying, pouring, etc.). The polymerizable composition may be cured to form a textured back. The textured back may be removed from the textured mold. A polymerizable composition may be used to couple the textured back to the prosthesis. For example, a mixture in the ratio of about 12.5 grams of LIM 6010A, about 12.5 grams of LIM 6010B, and about 3.5 grams of coloring agent may be used.

Figure 8:
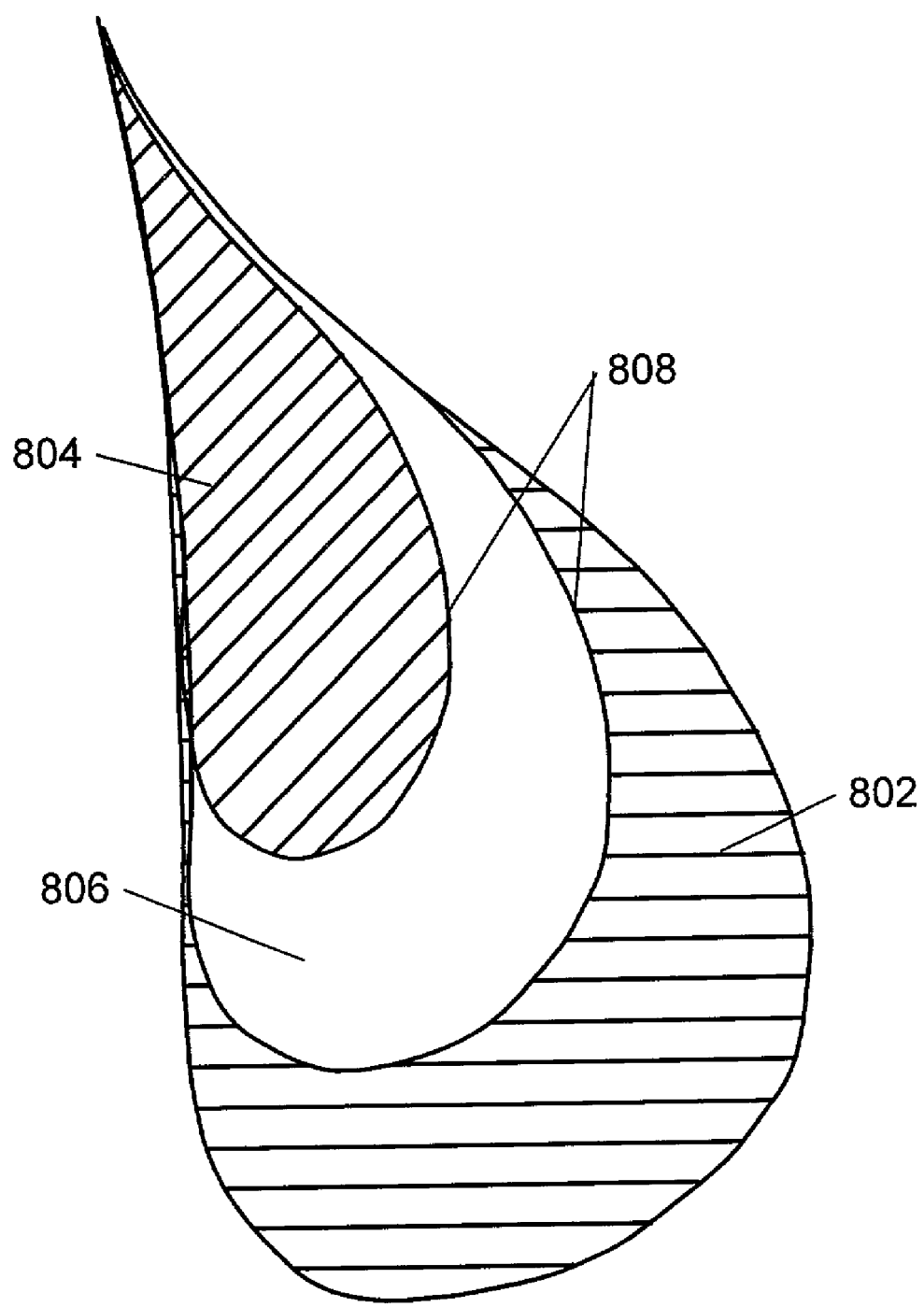
FIG. 8 depicts an embodiment of a breast prosthesis having multiple chambers.

In an embodiment, a breast prosthesis may include multiple chambers as depicted in FIG. 8. For example, a breast prosthesis may include an outer chamber 802, a back chamber 804, and one or more intermediate chambers 806. The chambers may be separated by one or more polymer layers 808. In an embodiment, the chambers may be cast separately, and then assembled. In an alternate embodiment, a first chamber may be cast. The first chamber may then be placed in a mold used to cast a second chamber during casting of the second chamber, and so on until a desired number of chambers are formed. The chambers may be filled with different materials to provide a realistic look and feel to the prosthesis. For example, outer chamber 802 may be filled with a gel material, back chamber 804 may be filled with a foam material, and an intermediate chamber 806 may be filled with air. Alternately, back chamber 804 may be filled with air and an intermediate chamber 806 may be filled with foam material. Other materials which may be used may include fluids of various densities and/or viscosities. Molds for forming the chambers may be formed as previously described. For example, a computer model of each chamber may be formed based on the computer model of the prosthesis. The chambers may be sized such that each chamber includes approximately one third of the prosthesis. However, depending on the patient's anatomy and the desired appearance of the prosthesis, each chamber may include significantly more or less of the prosthesis volume. For example, two chambers may include one quarter of the volume each, while the third chamber fills one half of the volume of the prosthesis. Additionally, more chambers may be used to form the prosthesis.

Typically, an external prosthetic device may be removably coupled to a patient. For example, a prosthesis may be removable coupled to a patient using adhesives. In an embodiment, a prosthetic may be formed with a retaining harness integral with the prosthesis. In another embodiment, an osseointegrated retaining device may be surgically implanted in a patient. A prosthesis may be coupled to the osseointegrated retaining device. In yet another embodiment, a prosthetic device may be coupled to a patient using one or more magnets adhesively coupled to a patient. In still another embodiment, a prosthetic device may be coupled to a patient using one or more male/female coupling devices, wherein at least one of the coupling devices is adhesively coupled to a patient.

Figure 9A:
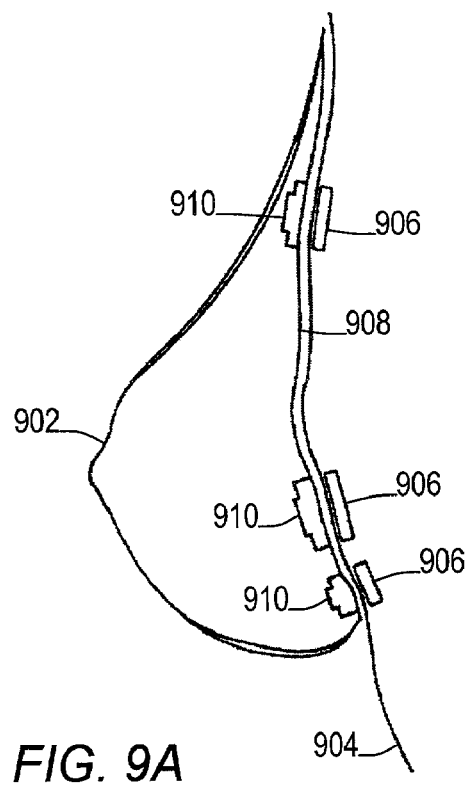
FIG. 9a depicts a side cutaway view of an embodiment of a breast prosthesis retained by a plurality of coupling devices.
Figure 9B:
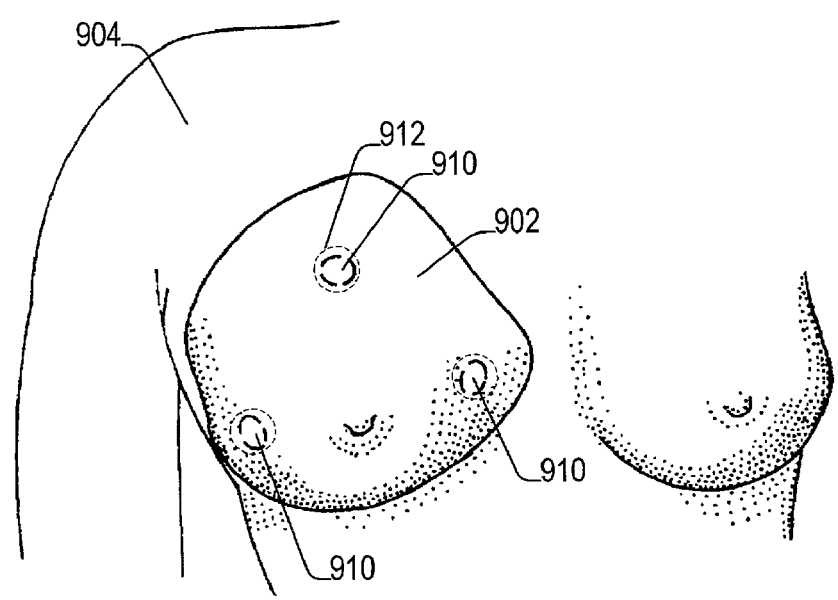
FIG. 9b depicts a front view of an embodiment of a breast prosthesis retained by a plurality of adhesively attached coupling devices.

FIGS. 9*a* and 9*b* depict an embodiment of a prosthetic device 902 coupled to a patient 904 by one or more coupling devices 906. In various embodiments, coupling devices 906 may include magnets and/or male coupling devices. Additionally, one or more coupling receptors 910 may be coupled to prosthetic device 902. In various embodiments, coupling receptors 910 may include metallic inserts and/or female receptors. Interaction of coupling devices 906 and coupling receptors 910 may act to retain prosthetic device 902 in relation to patient 904 during use. Prosthetic device 902 may include a textured backing 908 as previously described.

In an embodiment, coupling receptor 910 may be placed in a completed prosthesis 902 by preparing an opening 912 in the back of the prosthesis. For example, a surgical biopsy punch may be used to prepare the opening. Coupling receptor 910 may be placed in the prepared opening. Since the outer layer may be formed of a silicone material, if the coupling receptor includes a metallic insert, the metallic insert may be selected to be substantially free of sharp edges, especially on the portion facing the back. For example, the metallic insert may have a curved surface. If sharp edges are present, repeatedly placing and removing the prosthesis may cause the metallic insert to cut through the outer layer. A polymerizable composition may be used to seal coupling receptor 910 into opening 912. In an embodiment, the polymerizable composition used to form the outer layer may be used. For example, the polymerizable composition may include a mixture in the ratio of about 10 grams of LIM 6010A, about 10 grams of LIM 6010B, and about 5 grams of coloring agent. The polymerizable composition may be applied over the opening. In an embodiment, the polymerizable composition may flow past the edges of the coupling receptor to provide a secure seal. When the polymerizable composition has cured, the prosthesis may be ready for use.

Figure 10:
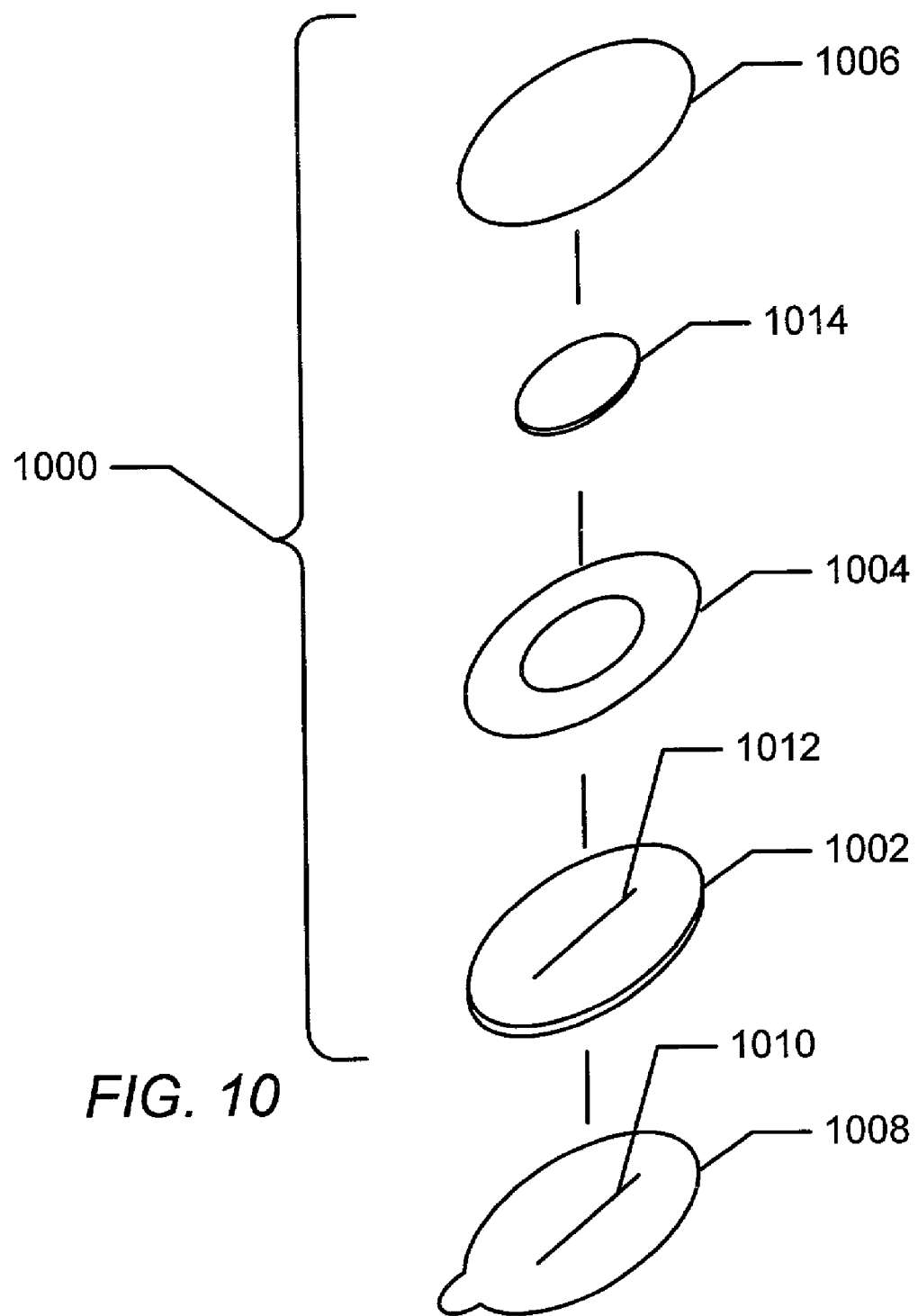
FIG. 10 depicts an exploded view of a pouch for coupling a magnet to a patient.

An embodiment of a coupling device is depicted in FIG. 10. As depicted in FIG. 10, a coupling device 906 may include a magnet 1014 disposed within a pouch 1000 for coupling a prosthetic device to a patient. Pouch 1000 may be formed to retain magnet 1014 and to adhere magnet 1014 to the patient. Pouch 1000 may include an adhesive-backed layer 1002, one or more intermediate layers 1004, and a top layer 1006. Additionally, pouch 1000 may be provided with a protective layer 1008, to cover the adhesive and inhibit accidental adhesion of the pouch during shipping, manufacture or handling of the pouch.

Top layer 1006 may provide added durability to the pouch, and act to retain magnet 1014 within the pouch. In an embodiment, top layer 1006 may include a polymer film. For example, a suitable top layer may include a polyurethane film. Alternately, a woven material may be used for top layer 1006. In an embodiment, top layer 1006 may include an opening through which magnet 1014 may be inserted into pouch 1000. In an alternate embodiment, openings (1012 and 1010) may be provided protective layer 1008 and adhesive-backed layer 1002 through which magnet 1014 may be inserted into pouch 1000.

Intermediate layer 1004 may include a spacer layer and/or an assembly layer. A spacer layer may provide added thickness to the pouch to ease inserting magnet 1014 into the pouch. A spacer layer may also help to distribute pressure from using the pouch over the patient's skin. An assembly layer may include an adhesive on each side, thus coupling top layer 1006 to adhesive-backed layer 1002. In an embodiment, intermediate layer 1004 may include a film having an adhesive on both sides. For example, 3M 9889 double coated tape, commercially available from Minnesota Mining and Manufacturing of St. Paul, Minn., may be used. In an alternate embodiment, no assembly layer may be used. In such a case, top layer 1006 may be coupled directly to adhesive-backed layer 1002. For example, adhesive may be applied to top layer 1006 or adhesive-backed layer 1002 to couple the layers. In another example, top layer 1006 may include an adhesive on its backside (e.g., the side that faces adhesive-backed layer 1002) to couple top layer 1006 to the adhesive-backed layer. In yet another example, adhesive-backed layer 1002 may include an adhesive layer on both sides. An advantage of including an assembly layer may be that adhesives may not contact magnet 1014 during use. Thus, magnet 1014 may be retained in pouch 1000 during use, and easily removed after use.

In an embodiment, adhesive-backed layer 1002 may include a foam medical tape. For example a polyethylene foam tape, such as 3M 9776 tape, may be used. 3M 9776 tape is commercially available from Minnesota Mining and Manufacturing of St. Paul, Minn. In such an embodiment, adhesive-backed layer 1002 may couple magnet 1014 to the patient, as well as provide some padding to the patient. Protective layer 1008 may be selected to be compatible with the adhesive of adhesive-backed layer 1002. Additionally, protective layer 1008 may be configured to make removal of protective layer 1008 relatively simple. For example, protective layer 1008 may include a pull-tab and/or a slit to make removing the protective layer easier.

In an embodiment, magnet 1014 may be composed of strong magnet, such as a permanent iron-boron-neodymium magnet. Such magnets are commercially available from Electron Energy Corporation of Landisville, Pa. Other magnetic materials that may be used include, but are not limited to, materials such as alnico, ferrite, barium ferrite, strontium ferrite, neodymium iron boron, samarium cobalt, iron oxide, or other ferromagnetic materials.

In an alternate embodiment, two layers of a polymer may encapsulate magnet 1014. Magnet 1014 may or may not be removable from between the polymer layers. For example, a polymer foam tape may be used to form a polymer layer. Bottom layer 1002 may include an adhesive for coupling pouch 1000 to the patient. In yet another embodiment, coupling receptor 910 may be magnetic. Thus, magnet 1014 may be implanted into the prosthesis and a metallic insert may be coupled to the patient. In still another embodiment, both coupling device 906 and coupling receptor 910 may include magnets.

In an embodiment, coupling device 906 and coupling receptor 910 may include complementary male and female shapes. For example, the coupling device and coupling receptor may form a ball and socket type joint. Other examples of suitable male and female couplers are described in U.S. Pat. Nos. 5,855,606 and 5,700,288, which are incorporated herein by reference as though fully set forth herein.

Figure 11B:
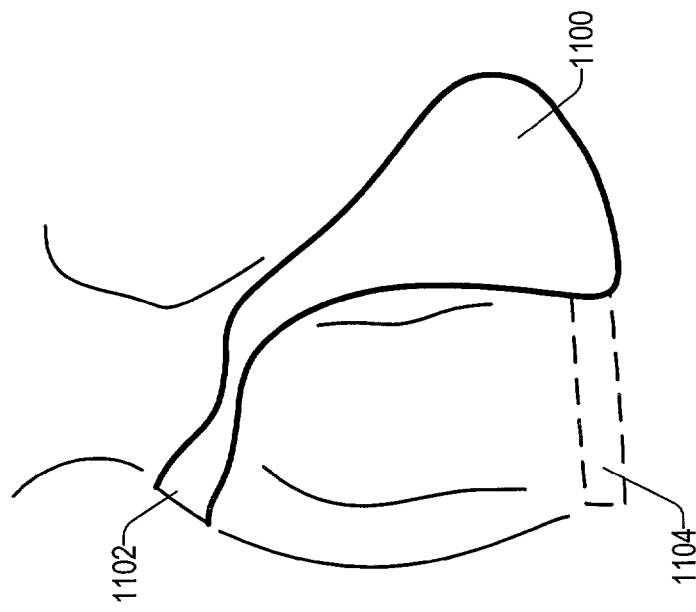
FIGS. 11a and 11b depict front and side views, respectively, of an embodiment of a prosthesis having an integral retaining device.
Figure 11A:
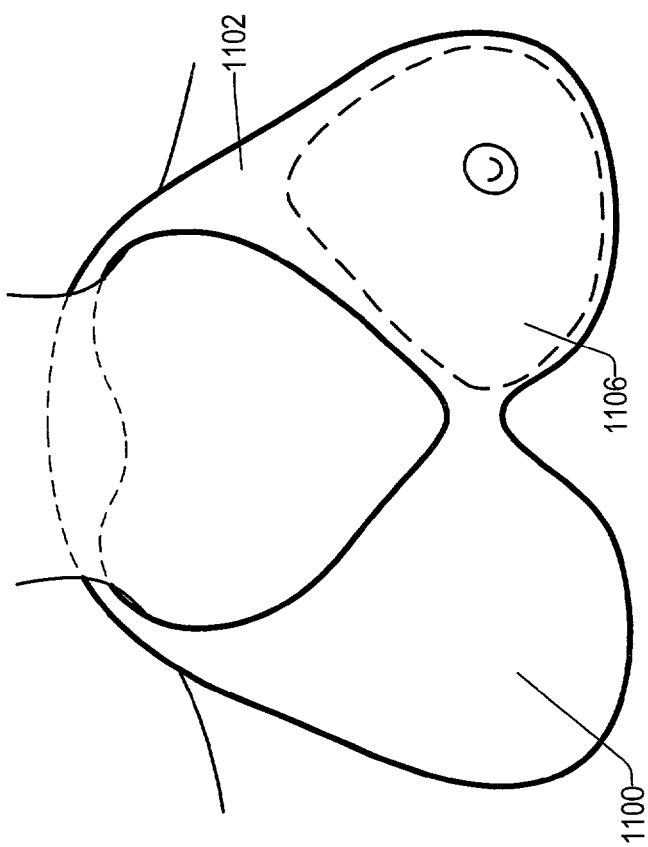

In an embodiment, a breast prosthesis 1100 may be formed with a retaining harness 1102 as depicted in FIGS. 11a and 11b. Retaining harness 1102 may be formed of one or more polymer layers, such as the polymer composition used to form the outer layer. Alternately, retaining harness 1102 may include a woven material. Retaining harness 1102 may be configured to be worn over the shoulders and behind the neck of the patient. In an embodiment, retaining harness 1102 may also include one or more straps 1104 that extend around the torso of the patient. If the patient has an intact breast, prosthesis 1100 may include an opening 1106 through which the intact breast may project. If a custom fit retaining harness 1102 is to be formed for a patient, the patient's back or entire upper torso may be scanned as previously described. A custom fit retaining harness 1102 may also be formed by forming an impression of the patient's anatomy, as is known in the art (e.g., with alginate, plaster, or other casting medium). Alternately, retaining harness 1102 may include one or more size adjustments. An advantage of prosthesis 1100 may be that it may be worn with or without a bra to provide a natural appearance to a patient.

Figure 12B:
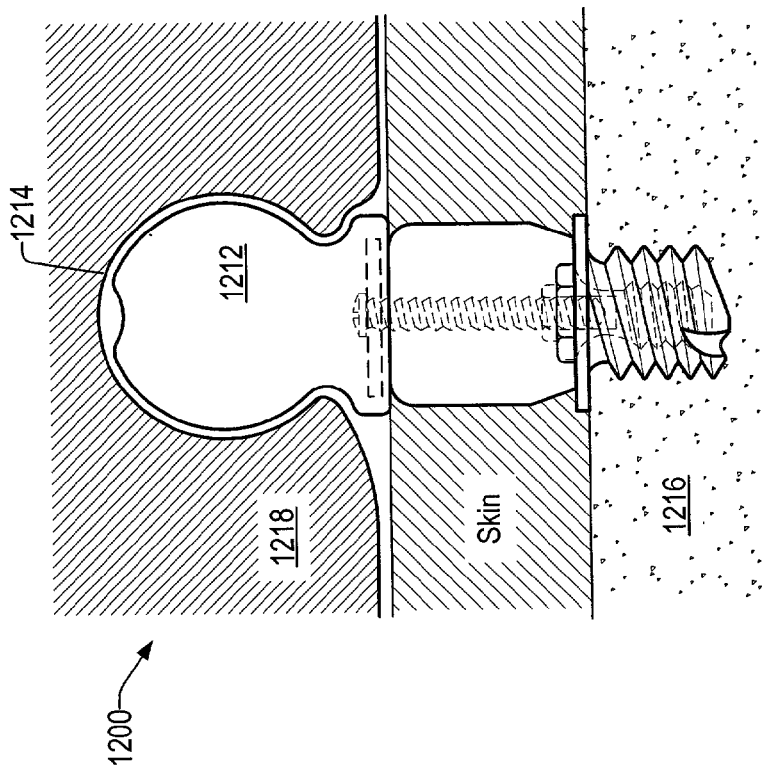
FIG. 12b depicts an assemble view of an embodiment of an osseointegrated prosthesis retaining device.
Figure 12A:
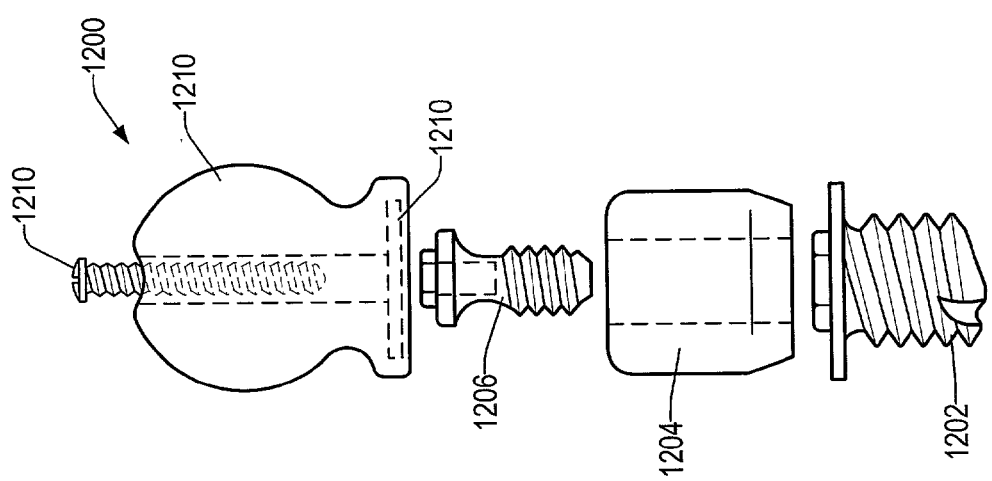
FIG. 12a depicts an exploded view of an embodiment of an osseointegrated prosthesis retaining device.

In an embodiment, a breast prosthesis may be retained in relation to a patient by use of an osseointergrated retaining device 1200, as depicted in FIGS. 12a and 12b. Osseointegrated retaining device 1200 may include a flange 1202, a percutaneous abutment connection 1204, a fixation connector 1206, a fixture mount 1208, and a retaining connector 1210. In an embodiment, flange 1202 and percutaneous abutment connection 1204 may be formed of biocompatible materials, such as, but not limited to: titanium, gold and/or surgical grade stainless steel. One or more flanges 1202 may be surgically implanted in a patient's rib 1216 (e.g., first, second, third, fourth or fifth costal). Percutaneous abutment connection 1204 may be coupled to flange 1202 using fixation connector 1206. Fixation connector 1206 may be configured to interact with retaining connector 1210 to retain fixture mount 1208. For example, fixation connector 1206 may include a threaded opening for receiving retaining connector 1210. However, it is recognized that other types of connectors (e.g., bayonette connectors, interlocking connectors, ratcheting connectors, adhesives, etc.) may also be used. Fixture mount 1208 may include an engaging member 1212 complementary to an engaging member 1214 of prosthesis 1220. Additionally, fixture mount 1208 may include reinforcing washer 1218. Reinforcing washer 1218 may be formed from a biocompatible material. During use, the patient may insert engaging member 1212 into engaging member 1214 of the prosthesis. Thus, prosthesis 1220 may be retained in position relative to the patient's body. Additionally, in some embodiment, the prosthesis may be free to move over a range of motion dependent on the shape of complementary engaging members.

While the present invention has been described with reference to particular embodiments, it will be understood that the embodiments are illustrated and that the invention scope is not so limited. For example, embodiments of an osseointegrated retaining device may be used to retain other types of prostheses. Additionally, scanning computer model forming techniques and/or solid model forming techniques as disclosed herein may be used with other prosthesis forming processes. Any variations, modifications, additions and improvements to the embodiments described are possible. These variations, modifications, additions and improvements may fall within the scope of the invention as detailed within the following claims.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

What is claimed is:

1. A method of forming a model of a breast prosthesis for a patient who has had one breast at least partially removed, comprising:

providing a scanning system comprising one or more imaging devices and one or more alignment markers, wherein at least one of the alignment markers comprises a tangible object, wherein the tangible object is noticeable in a scanned image and may be used to manipulate a scanned image as a reference point;

arranging at least one of the alignment markers in the middle of the body of the patient and within the field of view of at least one of the imaging devices;

determining a first set of data elements using the scanning system is based on a shape of the patient's intact breast;

determining a first computer model of the intact breast based on the first set of data elements;

using at least one of the alignment markers in the middle of the body of the patient as a fixed reference point relative to the patient to determine alignment of the first computer model of the intact breast;

applying a reflection transformation to the first computer model of the intact breast to form a second computer model, the second computer model comprising a second set of data points that represents a mirror image of the first computer model;

determining a third set of data elements using the scanning system based on a surgical site at which the breast was at least partially removed;

determining a third computer model based on the third set of data elements; and combining the third computer model and the second computer model to form a breast prosthesis model, wherein the second computer model defines an anterior portion of the breast prosthesis model that mirrors the intact breast and the third computer model defines a posterior portion of the breast prosthesis model that is custom fit to the surgical site.

2. A method of forming a model of a breast prosthesis for a patient who has had one breast at least partially removed, comprising:

provide a scanning system comprising one or more imaging devices and one or more alignment markers, wherein at least one of the alignment markers comprises a tangible object, wherein the tangible object is noticeable in a scanned image and may be used to manipulate a scanned image as a reference point;

arranging at least one of the alignment markers in the middle of the body of the patient and within the field of view of at least one of the imaging devices;

determining a first set of data elements using the scanning system based on a shape of a garment at least partially covering the patient's intact breast;

determining a computer model of a breast prosthesis based on the first set of data elements; and using at least one of the alignment markers in the middle of the body of the patient as a fixed reference point relative to the patient to determine alignment of the first computer model;

applying a reflection transformation to the first computer model of the garment covering the intact breast to form a second computer model, the second computer model comprising a second set of data points that represents a mirror image of the first computer model;

determining a third set of data elements using the scanning system based on a surgical site at which the breast was at least partially removed;

determining a third computer model based on the third set of data elements; and combining the third computer model and the second computer model to form a breast prosthesis model, wherein the second computer model defines an anterior portion of the breast prosthesis model that substantially mirrors the intact breast and the third computer model defines a posterior portion of the breast prosthesis model that is custom fit to the surgical site.

3. The method of claim 1, further comprising storing the computer model on a memory medium.

4. The method of claim 1, wherein the scanning system further comprises an orientation marker, wherein the orientation marker is a tangible object.

5. The method of claim 1, wherein the scanning system further comprises an orientation marker, wherein the orientation marker may be used to orient the patient relative to one of the one or more imaging devices or to orient one of the one or more imaging devices relative to the patient, and wherein the method further comprises arranging the orientation marker with respect to the patient and within the field of view of at least one of the imaging devices, and determining whether the imaging device and the patient are properly oriented relative to each other using the orientation marker.

6. The method of claim 1, wherein the first set of data elements is based on the shape of the patient's breast while the breast is at least partially covered by a garment.

7. The method of claim 1, wherein determining the computer model of the breast prosthesis based on the first set of data elements comprises modifying the first set of data elements to remove data elements corresponding to a garment at least partially covering the patient's breast.

8. The method of claim 1, wherein determining the first set of data elements comprises sweeping light from one or more light sources over a portion of the patient's anatomy comprising at least the patient's breast and detecting reflected light, wherein at least one of the alignment markers reflects light more strongly than the patient's skin.

9. The method of claim 1, wherein determining the first set of data elements comprises sweeping light from one or more light sources over a portion of the patient's anatomy comprising the at least the patient's breast and detecting reflected light, wherein at least one of the alignment markers reflects light less strongly than the patient's skin.

10. The method of claim 1, wherein the scanning system further comprises one or more orientation markers, wherein at least one of the orientation markers comprises an elongated member.

11. The method of claim 2, wherein the garment comprises a bra cup filled with a breast form.

12. The method of claim 2, further comprising shaping the garment to a desired shape before determining the first set of data elements.

13. The method of claim 2, further comprising storing the computer model on a memory medium.

14. The method of claim 2, wherein the scanning system further comprises an orientation marker, wherein the orientation marker is a tangible object.

15. The method of claim 2, wherein the scanning system further comprises an orientation marker, wherein the orientation marker may be used to orient the patient relative to one of the one or more imaging devices or to orient one of the one or more imaging devices relative to the patient, and wherein the method further comprises arranging the orientation marker with respect to the patient and within the field of view of at least one of the imaging devices and determining whether the imaging device and the patient are properly oriented relative to each other using the orientation marker.

16. The method of claim 1, wherein at least one of the alignment markers is placed substantially directly below the suprasternal notch.

17. The method of claim 2, wherein at least one of the alignment markers is placed substantially directly below the suprasternal notch.

18. The method of claim 1, further comprising determining orientation in the first computer model, wherein determining orientation in the first computer model comprises determining a shape of at least one orientation markers in the first computer model.

19. The method of claim 5, further comprising re-determining the first set of data elements using the scanning system if at least of the imaging devices and the patient are determined not to be properly oriented relative to one another using the orientation marker.

20. The method of claim 15, further comprising re-determining the first set of data elements using the scanning system if at least of the imaging devices and the patient are determined not to be properly oriented relative to one another using the orientation marker.

21. The method of claim 5, further comprising a using a scanned image of the orientation marker in a graphics manipulation software application to remove undesired perspective if at least of the imaging devices and the patient are determined not to be properly oriented relative to one another using the orientation marker.

22. The method of claim 15, further comprising a using a scanned image of the orientation marker in a graphics manipulation software application to remove undesired perspective if at least of the imaging devices and the patient are determined not to be properly oriented relative to one another using the orientation marker.

23. The method of claim 5, further comprising orienting at least one of the imaging devices or the patient after determining whether the imaging device and the patient are properly oriented relative to each other.

24. The method of claim 15, further comprising orienting at least one of the imaging devices or the patient after determining whether the imaging device and the patient are properly oriented relative to each other.

25. The method of claim 1, wherein applying a reflection transformation to the first computer model of the intact breast to form a second computer model comprises:
   identifying a perimeter of the first computer model to establish an edge of a breast form; and
   taking a depth measurement based on the perimeter; and
   using the depth measurement to ensure symmetry of the first computer model and the second computer model.

26. The method of claim 1, further comprising adjusting the posterior portion of the breast prosthesis model to provide clearance over at least one sensitive area of a patient such that the prosthesis will not contact the sensitive area of the patient.

27. The method of claim 2, wherein applying a reflection transformation to the first computer model to form a second computer model comprises:
   identifying a perimeter of the first computer model to establish an edge of a breast form; and
   taking a depth measurement based on the perimeter; and
   using the depth measurement to ensure symmetry of the first computer model and the second computer model.

28. The method of claim 2, further comprising adjusting the posterior portion of the breast prosthesis model to provide clearance over at least one sensitive area of a patient such that the prosthesis will not contact the sensitive area of the patient.

29. The method of claim 2, further comprising manipulating the breast prosthesis model to form desired features.

30. The method of claim 2, further comprising manipulating the breast prosthesis model to remove undesired features, wherein removing the undesired features comprises removing lines of a garment from the model.

* * * * *